US00PP24035P3

(12) United States Plant Patent

Klemm et al.

(10) Patent No.: US PP24,035 P3

(45) Date of Patent: Nov. 19, 2013

(54) *CALIBRACHOA* PLANT NAMED 'KLECA11227'

(50) Latin Name: ***Calibrachoa* sp.**
Varietal Denomination: KLECA11227

(75) Inventors: Nils Klemm, Stuttgart (DE); Anita Stöver, Ostfildern (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 96 days.

(21) Appl. No.: 13/506,067

(22) Filed: Mar. 23, 2012

(65) Prior Publication Data

US 2013/0254961 P1 Sep. 26, 2013

(51) Int. Cl.
*A01H 5/00* (2006.01)

(52) U.S. Cl.
USPC ..... Plt./413

(58) Field of Classification Search
USPC ..... Plt./413
See application file for complete search history.

*Primary Examiner* — Susan McCormick Ewoldt

(74) *Attorney, Agent, or Firm* — Jondle Plant Sciences Division of Swanson & Bratschun, L.L.C.

(57) ABSTRACT

A new *calibrachoa* plant named 'KLECA11227' particularly distinguished by large orange flowers and very healthy leaves is disclosed.

1 Drawing Sheet

Genus and species: *Calibrachoa* sp.
Variety denomination: 'KLECA11227'.

BACKGROUND OF THE NEW PLANT

The present invention comprises a new and distinct variety of *calibrachoa*, botanically known as *Calibrachoa* sp. and hereinafter referred to by the variety name 'KLECA11227'. The new variety was the result of a controlled cross conducted in the summer of 2008 in Stuttgart, Germany, between the female parent *calibrachoa* plant 'CA 05 0283 M.F. Watermelon' (unpatented), and the male parent *calibrachoa* plant 'J 903' (unpatented). A single plant selection was subsequently chosen for further evaluation and asexual propagation.

The new variety was first propagated by vegetative cuttings and in vitro propagation in May 2009 in Stuttgart, Germany and has been asexually reproduced repeatedly by vegetative cuttings for more than 80 generations. The present invention has been found to retain its distinctive characteristics through successive asexual propagations via vegetative cuttings.

Plant Breeder's Rights for 'KLECA11227' were applied for in Canada on Jan. 18, 2012. 'KLECA11227' has not been made publicly available or sold more than one year prior to the filing date of this application.

SUMMARY OF THE INVENTION

The following are the most outstanding and distinguishing characteristics of this new variety when grown under normal horticultural practices in a glass greenhouse in Stuttgart, Germany.

1. Large orange flowers; and
2. Very healthy leaves.

DESCRIPTION OF THE PHOTOGRAPH

This new *calibrachoa* plant is illustrated by the accompanying photograph which shows inflorescences and foliage of the plant. The colors shown are as true as can be reasonably obtained by conventional photographic procedures.

The photograph was taken in May 2011 of a 5-month old *calibrachoa* plant grown in an 11 centimeter pot in a glass greenhouse in Stuttgart, Germany under normal horticultural practices.

DESCRIPTION OF THE NEW VARIETY

The following detailed descriptions set forth the distinctive characteristics of 'KLECA11227'. The data which defines these characteristics were collected from asexual reproductions carried out in Stuttgart, Germany. The plant history was taken in May 2011 of 5-month old plants grown in 11 centimeter pots in a glass greenhouse. Plants were pinched once at week 10. Color readings were taken under artificial light at an illumination of approximately 20 Klx. Color references are primarily to The R.H.S. Colour Chart of The Royal Horticultural Society of London (R.H.S.), Fifth Edition (2007).

DETAILED BOTANICAL DESCRIPTION OF THE NEW PLANT

Classification:
- *Family.*—Solanaceae.
- *Botanical.*—*Calibrachoa* sp.
- *Common.*—*Calibrachoa.*
- *Denomination.*—'KLECA11227'.

Parentage:
- *Female.*—*Calibrachoa* plant 'CA 05 0283 M.F. Watermelon' (unpatented).
- *Male.*—*Calibrachoa* plant 'J 903' (unpatented).

Growth:
- *Form.*—Uniformly mounded.
- *Habit.*—Upright to cascading.
- *Height* (*measured from the top of the soil*).—14.0 cm.
- *Width* (*horizontal plant diameter*).—16.0 cm.
- *Time to produce a finished flowering plant.*—7 weeks after potting.

*Outdoor plant performance.*—Very healthy, continuous flowering.
*Time to initiate and develop roots.*—21 days.
*Root description.*—Moderate density, freely branching, fine and fibrous.
*Root color.*—RHS 155 D.

Stems:
*Length of basal branches.*—8.0 cm.
*Internode length.*—2.0 cm.
*Diameter of branches* (*from midpoint*).—9.0 cm.
*Stem color.*—RHS 144B.
*Texture.*—Smooth.
*Anthocyanin.*—Absent.
*Pedicel.*—Color: RHS 144A. Length: 1.3 cm. Diameter: 0.1 cm. Texture: Smooth.

Leaves:
*Arrangement.*—Alternate.
*Length.*—2.5 cm.
*Width.*—0.9 cm.
*Shape.*—Lanceolate to elliptic.
*Apex.*—Obtuse to slightly acute.
*Base.*—Attenuate.
*Margin.*—Entire.
*Color* (*both immature and mature leaves*).—Upper surface: RHS 137B. Lower surface: RHS 137D.
*Texture* (*both surfaces*).—Smooth.
*Venation pattern.*—Pinnate.
*Venation color.*—RHS 138B.
*Petioles.*—Absent.

Flower bud:
*Shape.*—Irregular to oblong.
*Length.*—1.9 cm.
*Diameter.*—0.6 cm.
*Color at tight bud.*—RHS 174C.

Inflorescence:
*Blooming habit.*—Continuous; axillary flowers face upwards.
*Inflorescence type.*—Single flower, determinate inflorescence.
*Floret type.*—Funnel-shaped, single flowers.
*Lastingness of individual blooms on the plant.*—6 days.
*Fragrance.*—Absent.

Flowers:
*Immature flower.*—Width: 2.4 cm. Length: 1.7 cm. Color: Upper surface: RHS N25B. Lower surface: RHS 25D.
*Mature flower.*—Width: 2.9 cm. Length: 2.3 cm. Color: Upper surface: RHS N25B. Lower surface: RHS 25D.
*Corolla tube.*—Color inside: RHS 13B. Color outside: RHS 11B. Tube length: 1.6 cm. Texture (inside & outside): Smooth.
*Petals.*—Apex: Obverse. Base: Open and fused into a tube. Margin: Entire. Waviness of petals: Very weak. Lobation: Weak. Texture (both surfaces): Smooth.
*Sepals.*—Calyx (composition): Actinomorphic. Shape: Lanceolate to elliptic. Apex: Acute. Base: Open and tube is fused into the base. Margin: Entire. Length: 1.4 cm. Width: 0.3 cm. Color: Upper surface: RHS 137A. Lower surface: RHS 137C. Texture (both surfaces): Smooth.

Reproductive organs:
*Stamens.*—Quantity: 5. Filament color: RHS 1D. Filament length: 1.0 cm. Filament diameter: 0.1 cm. Anther color: RHS 1D. Pollen color: RHS 15B. Pollen quantity: Sparse.
*Pistils.*—Quantity: 1. Length: 0.8 cm. Diameter: 0.1 cm. Stigma color: RHS 1B. Style color: RHS 154A.

Fruit and seed set: No fruit or seed set observed.

Disease and insect resistance: No particular resistance to disease or pests observed.

COMPARISON WITH PARENTAL AND COMMERCIAL VARIETIES

'KLECA11227' differs from the female parent *calibrachoa* plant 'CA 05 0283 M.F. Watermelon', (unpatented) in that 'KLECA11227' has orange colored flowers, whereas 'CA 05 0283 M.F. Watermelon' has red colored flowers.

'KLECA11227' differs from the male parent *calibrachoa* plant 'J 903' (unpatented) in that 'KLECA11227' has orange (RHS N25B) colored flowers, whereas 'J 903' has greyed-orange (RHS N163B) colored flowers.

'KLECA11227' differs from the commercial cultivar, 'KLECA08187' (U.S. Plant Pat. No. 21,020), in that 'KLECA11227' has orange colored flowers of RHS N25B, whereas 'KLECA08187' has yellow-orange and red colored flowers of RHS 15B and RHS 43B. Additionally, 'KLECA08187' is sensitive to pH variation and becomes chlorotic, whereas 'KLECA11227' is not sensitive to pH variation.

We claim:

1. A new and distinct variety of *calibrachoa* plant named 'KLECA11227' as shown and described herein.

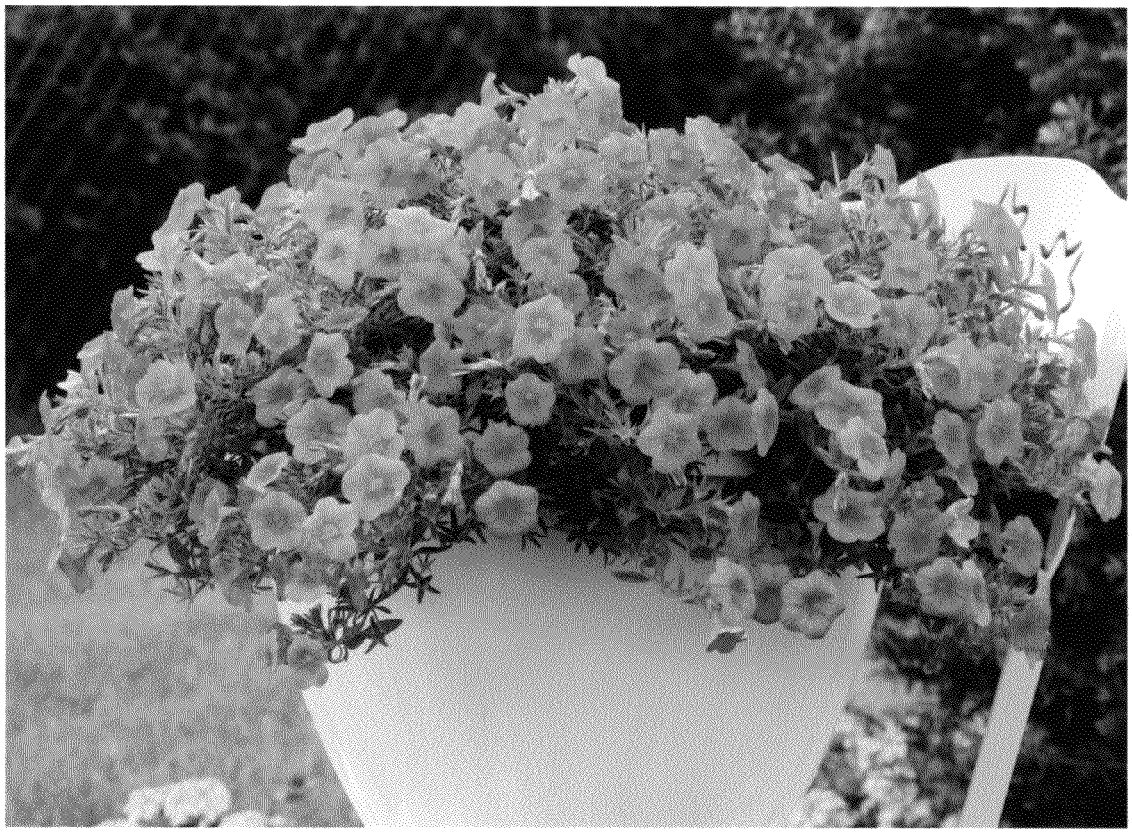

* * * * *